(12) United States Patent
Hong et al.

(10) Patent No.: US 10,426,329 B2
(45) Date of Patent: Oct. 1, 2019

(54) MULTIPURPOSE SELF-ILLUMINATING DENTAL MIRROR

(71) Applicants: Brian KwangShik Hong, Los Angeles, CA (US); Jin H. Yang, Wilmington, CA (US)

(72) Inventors: Brian KwangShik Hong, Los Angeles, CA (US); Jin H. Yang, Wilmington, CA (US)

( * ) Notice: Subject to any disclaimer, the term of this patent is extended or adjusted under 35 U.S.C. 154(b) by 16 days.

(21) Appl. No.: 15/735,191

(22) PCT Filed: Jul. 23, 2016

(86) PCT No.: PCT/US2016/043777
§ 371 (c)(1),
(2) Date: Dec. 10, 2017

(87) PCT Pub. No.: WO2017/015645
PCT Pub. Date: Jan. 26, 2017

(65) Prior Publication Data
US 2018/0177389 A1  Jun. 28, 2018

Related U.S. Application Data

(60) Provisional application No. 62/195,811, filed on Jul. 23, 2015.

(51) Int. Cl.
*A61B 1/24* (2006.01)
*A61B 1/247* (2006.01)
(Continued)

(52) U.S. Cl.
CPC .......... *A61B 1/247* (2013.01); *A61B 1/00032* (2013.01); *A61B 1/00124* (2013.01);
(Continued)

(58) Field of Classification Search
CPC ......... A61B 1/247; A61B 1/0684; A61B 1/24; A61C 1/088; A61C 19/04
See application file for complete search history.

(56) References Cited

U.S. PATENT DOCUMENTS 3,638,013 A * 1/1972 Keller ...................... A61B 1/07
                                                            362/120
4,279,594 A * 7/1981 Rigutto .................. A61B 1/253
                                                            433/31
(Continued)

OTHER PUBLICATIONS

International Search Report and Written Opinion for PCT/US2016/043777, dated Oct. 18, 2016.

*Primary Examiner* — Ralph Lewis
(74) *Attorney, Agent, or Firm* — John R. Kasha; Kelly L. Kasha; Kasha Law LLC

(57) ABSTRACT

A multipurpose self-illuminating dental mirror is made up of three detachable assemblies. A first assembly includes a head and shank. The head has a mirrored forward surface and a rear transparent surface that includes one or more rear-facing light sources. The shank is connected to the head at an angle and has one or more forward-facing light sources extending from the shank at the connection of the shank with the head. The light sources of the first assembly are used to provide illumination for the mirrored forward surface of the first assembly. The second assembly includes a handle that encloses one or more batteries used to power the light sources of the first assembly. The third assembly includes a laser pointer and a housing for a pen or stylus. The one or more batteries of the second assembly are also used to power the laser pointer.

15 Claims, 7 Drawing Sheets

(51) Int. Cl.
*A61B 1/06* (2006.01)
*A61C 3/00* (2006.01)
*A61B 1/00* (2006.01)
*G06F 3/0354* (2013.01)

(52) U.S. Cl.
CPC .............. *A61B 1/06* (2013.01); *A61B 1/0684* (2013.01); *A61C 3/00* (2013.01); *A61C 2204/002* (2013.01); *G06F 3/03545* (2013.01)

(56) References Cited

U.S. PATENT DOCUMENTS

| | | | | |
|---|---|---|---|---|
| 4,629,425 | A * | 12/1986 | Detsch | A61B 1/253 433/29 |
| 4,993,945 | A * | 2/1991 | Kimmelman | A61B 1/247 219/219 |
| 5,139,420 | A * | 8/1992 | Walker | A61B 1/253 433/31 |
| 5,139,421 | A * | 8/1992 | Verderber | A61B 1/247 433/30 |
| 5,741,132 | A * | 4/1998 | Usui | A61B 1/253 433/30 |
| 6,276,934 | B1 * | 8/2001 | Rakocz | A61B 1/247 433/29 |
| 6,443,729 | B1 * | 9/2002 | Watson | A61B 1/253 433/116 |
| 6,544,036 | B1 * | 4/2003 | Brattesani | A61B 1/247 433/29 |
| 8,172,571 | B2 * | 5/2012 | Watson | A61B 1/253 433/31 |
| 2005/0026104 | A1 * | 2/2005 | Takahashi | A61B 1/247 433/31 |

* cited by examiner

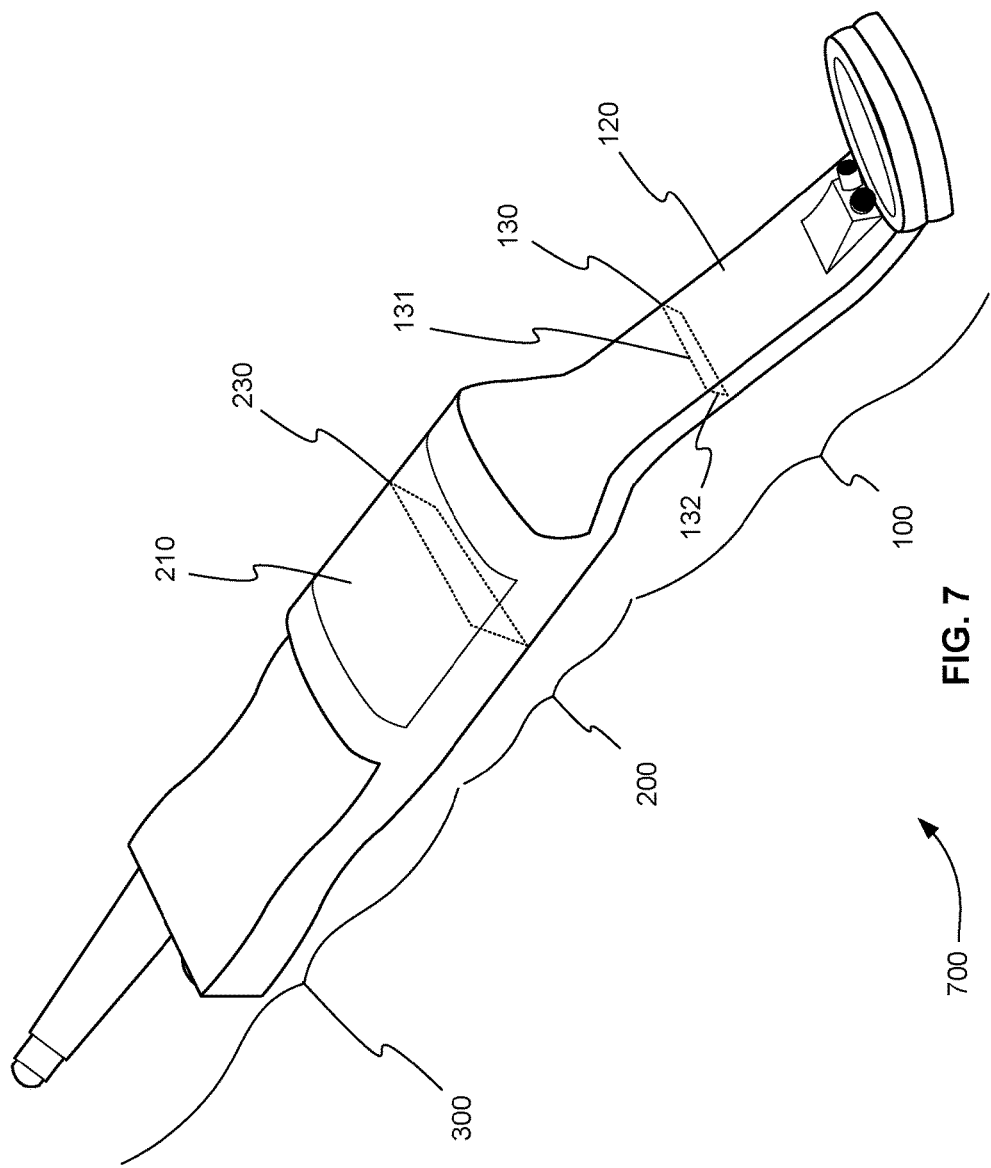

MULTIPURPOSE SELF-ILLUMINATING DENTAL MIRROR

CROSS-REFERENCE TO RELATED APPLICATION

This application claims the benefit of U.S. Provisional Patent Application No. 62/195,811 filed Jul. 23, 2015, which is incorporated in its entirety by reference herein.

INTRODUCTION

Hand-held medical instruments such as dental mirrors have long been known and used the clinical field of dentistry. Dental mirrors allow clinicians to view various parts of the mouth and throat (if used with an extension) that may be difficult or impossible to see by a direct line of sight. However, some parts of the mouth are difficult to see even with the aid of a dental mirror. The lighting conditions inside of a patient's mouth are often poor, at best. A dark dental mirror is often of limited use. Therefore, over the years, the dental industry has sought to develop a mirror with its own illumination system rather than depending on the light available from an overhead lamp. Examples of such mirrors are disclosed in U.S. Pat. No. 3,638,013 to Keller; U.S. Pat. No. 4,279,594 to Rigutto; U.S. Pat. No. 4,629,425 to Detsch; U.S. Pat. No. 4,993,945 to Kimmelman et al.; U.S. Pat. No. 5,139,420 to Walker; U.S. Pat. No. 5,139,421 to Verderber; U.S. Pat. No. 5,457,611 to Verderber; U.S. Pat. No. 6,443,729 to Watson; and U.S. Pat. No. 8,172,571 to Watson.

Although these mirrors have included their own light source, they have generally fallen short. Most of these dental mirrors only use a single light source so a dentist can only see limited lighted area inside of a patient's mouth. Therefore, the dentist still needs external lighting to effectively treat the patient. A need exists for improved dental mirrors for both patients and dentists for safe and better treatment of patients.

BRIEF DESCRIPTION OF THE DRAWINGS

FIG. 7 is a perspective view of a multipurpose self-illuminating dental mirror, in accordance with various embodiments.

Before one or more embodiments of the invention are described in detail, one skilled in the art will appreciate that the invention is not limited in its application to the details of construction, the arrangements of components, and the arrangement of steps set forth in the following detailed description. The invention is capable of other embodiments and of being practiced or being carried out in various ways. Also, it is to be understood that the phraseology and terminology used herein is for the purpose of description and should not be regarded as limiting.

DETAILED DESCRIPTION

Dental Mirror

As noted above, dentists have found that conventional dental mirrors are inconvenient to use during treatment of patients, and a need exists for improved dental mirrors for both patients and dentists for safe and better treatment of patients.

An embodiment of a dental mirror with improved illumination uses a larger mirror so that a dentist can better view the inside of a patient's mouth. Also, the body of the dental mirror is wider than a conventional dental mirror for better grip and to enable the dentist to retract the patient's cheek and tongue with less strain to the dentist's hand and fingers.

Also, an embodiment of the dental mirror with improved illumination uses three lighting sources on the dental mirror. As a result, the dental mirror provides more illuminated area inside of a patient's mouth.

In various embodiments, one of the light sources is mounted on the back side of the dental mirror for providing illumination to the back side of the dental mirror.

In various embodiments, the dental mirror uses small size direct-current (DC) batteries, including AA and AAA alkaline batteries, which are readily available and cost efficient. In various embodiments, the dental mirror uses light-emitting diodes (LEDs) as its lighting sources, which are also conveniently available in the market. In various embodiments, the dental mirror consumes a small amount of power and the battery can last more than 50 hours with continuous use.

In various embodiments, the dental mirror can include, in addition to the mirror function, one or more of a ball point pen, capacitive stylus, and presentation pointer. One skilled in the art will appreciate that other functions can be similarly provided on the dental mirror. These functions provide great convenience for dentists to treat and help their patients.

Figure 1:
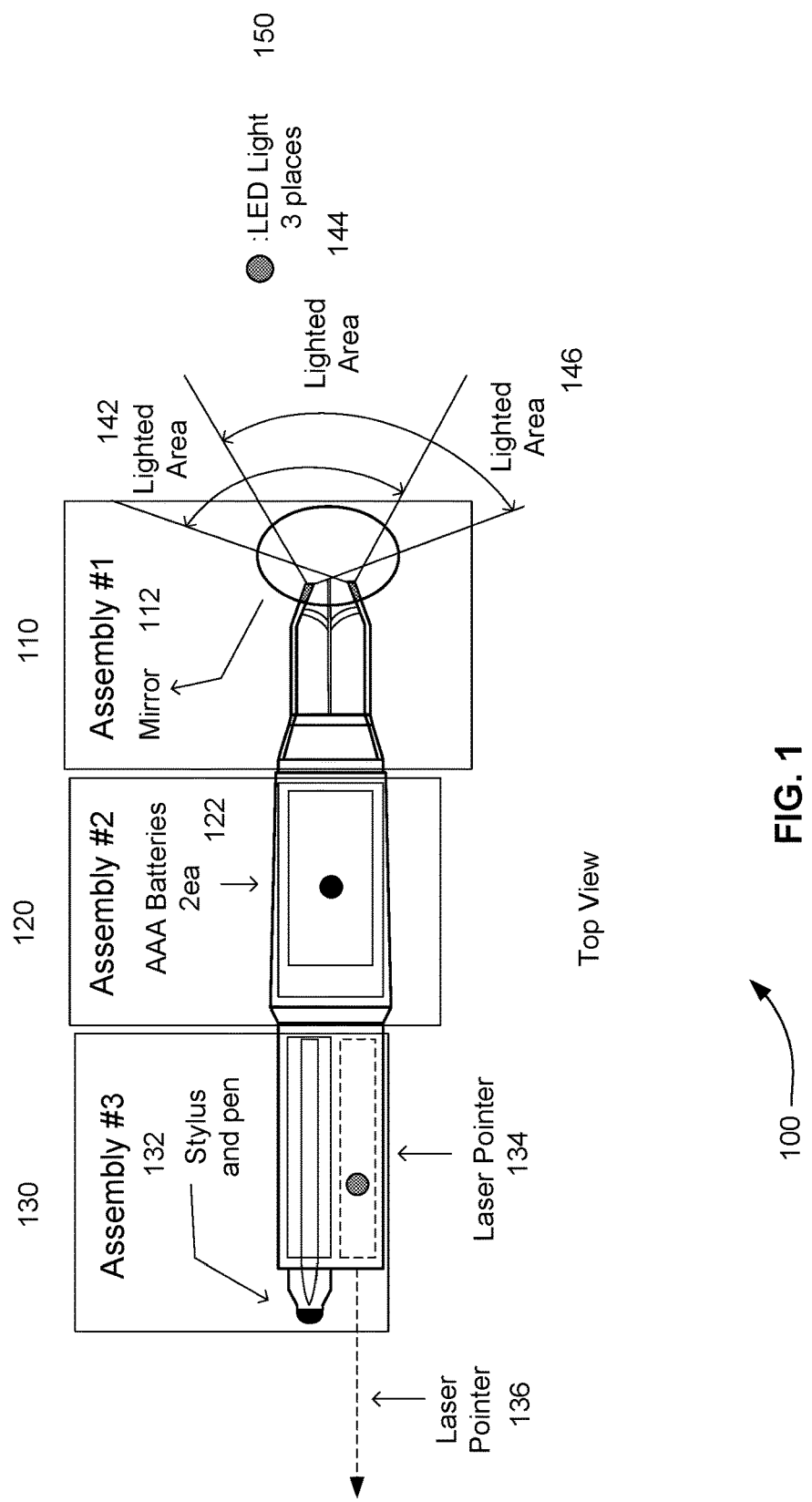
FIG. 1 is a top view of an embodiment of a dental mirror with improved illumination, in accordance with various embodiments.

FIG. 1 is a top view 100 of an embodiment of a dental mirror, in accordance with various embodiments. The dental mirror includes, for example, three assemblies, assembly #1, 110, assembly #2, 120, and assembly #3, 130.

In various embodiments, Assembly #1, 110 is a pressure safe illumination unit. This unit 110 will pass a 135 C. degree sanitary test standard. Unit 110 includes mirror 112, three LED lights 150, and associated wiring.

In various embodiments, mirror 112 is larger than a conventional dental mirror.

In various embodiments, LED lights 150 are located in three places in unit 110, for example, to provide illumination in areas 142, 144, 146. One skilled in the art will appreciate that different numbers of LED lights can be provided on the dental mirror in various locations.

In various embodiments, Assembly #2, 120 is a direct-current (DC) power source unit that includes a compartment for batteries 122, such as two AAA alkaline batteries.

In various embodiments, batteries 122 may last over 50 hours for a continuous use.

In various embodiments, Assembly #3, 130 is a unit that provides additional functionalities, such as ball point pen and capacitive stylus 132, and laser presentation pointer 134 to a monitor (not shown) through line 136. One skilled in the art will appreciate that other functionalities can equally be provided on the dental mirror.

Figure 2:
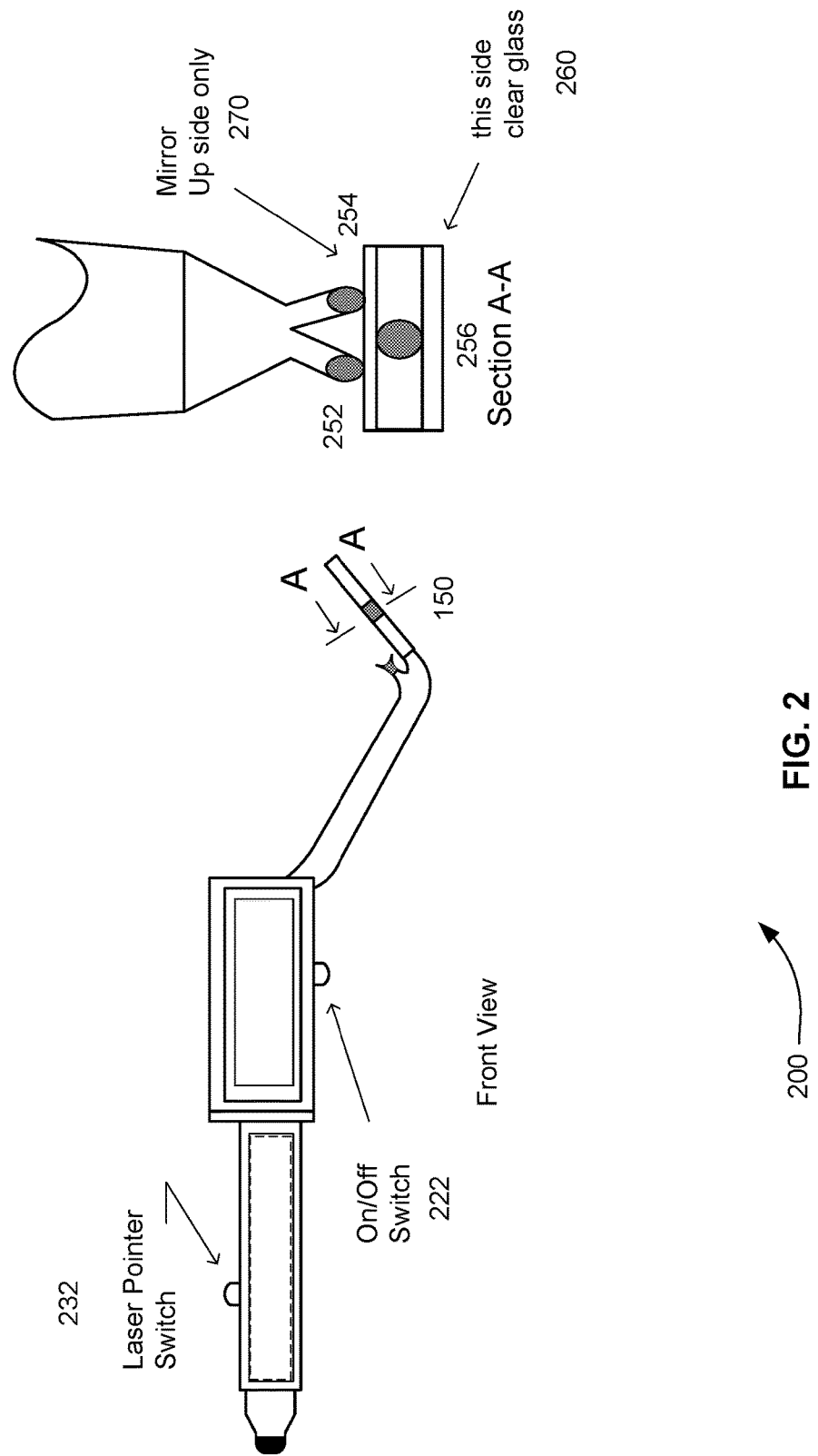
FIG. 2 is a front view of an embodiment of the dental mirror with improved illumination, in accordance with various embodiments.

FIG. 2 is a front view 200 of an embodiment of a dental mirror, in accordance with various embodiments.

In various embodiments, the dental mirror includes on/off switch 222 for turning LED lights 150 on and off.

In various embodiments, the dental mirror includes laser pointer switch 232 for turning laser pointer 134 on and off.

Section A-A of FIG. 2 shows LED lights 150 in more detail. A mirror is located on up-side 270. The bottom side 260 is made of clear glass. Three LED lights are shown as 252, 254, and 256.

Figure 3:
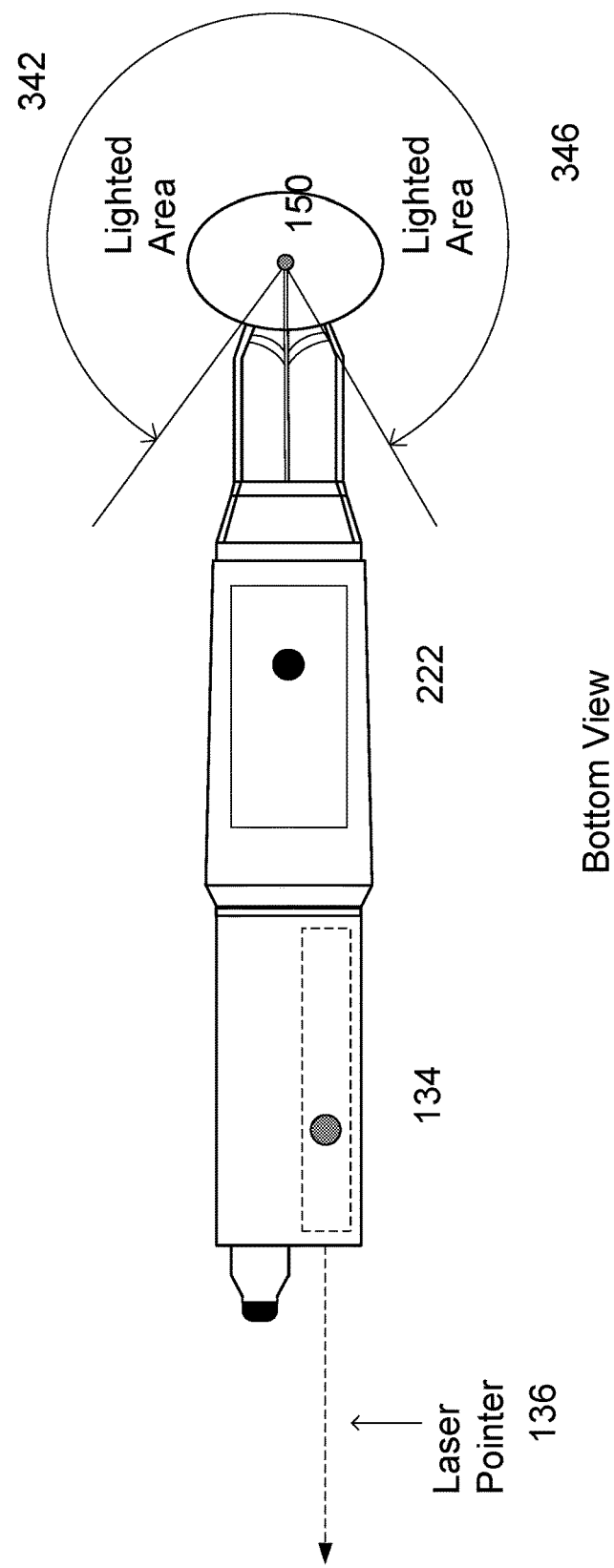
FIG. 3 is a bottom view of an embodiment of the dental mirror with improved illumination, in accordance with various embodiments.

FIG. 3 is a bottom view 300 of an embodiment of a dental mirror, in accordance with various embodiments. Similar to FIG. 1, laser pointer 134 points to a monitor (not shown) along line 136.

In various embodiments, LED lights 150 provide illumination in areas 342 and 346.

Figure 4:
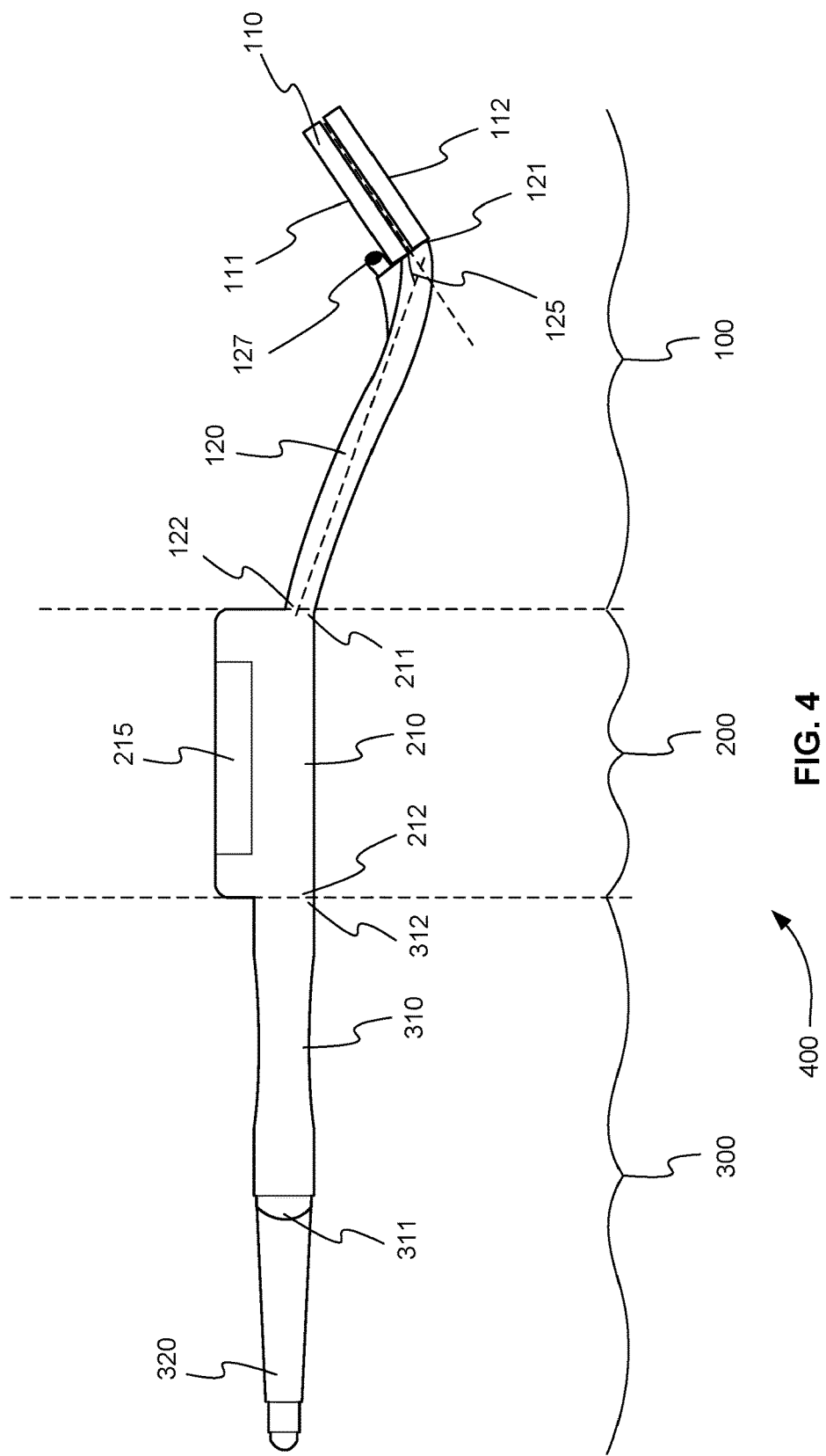
FIG. 4 is a side view of a multipurpose self-illuminating dental mirror, in accordance with various embodiments.

FIG. 4 is a side view 400 of a multipurpose self-illuminating dental mirror, in accordance with various embodiments. The multipurpose self-illuminating dental mirror includes first assembly 100, second assembly 200, and third assembly 300.

First assembly 100 includes head 110 and shank 120. Head 110 has mirrored forward surface 111 and rear transparent surface 112. Rear transparent surface 112 includes one or more rear-facing light sources (not shown). Shank 120 is physically connected at first end 121 to a side of head 110. Shank 120 extends longitudinally at an angle 125 from the plane of head 110. Shank 120 includes one or more forward-facing light sources 127 extending from shank 120 at the connection of shank 120 with the head 110. First assembly 100 also includes wiring (not shown) from the one or more rear-facing light sources and one or more forward-facing light sources 127 that extends through shank 120 to a first electrical connector (not shown) at second end 122 of shank 120.

Second assembly 200 includes a handle 210. Handle 210 includes a housing 215 for housing one or more batteries (not shown). Second assembly 200 includes wiring that electrically connects the one or more batteries to a second electrical connector at first end 211 of handle 210 and a third electrical connector (not shown) at second end 212 of handle 210. The one or more batteries can include one or more AAA batteries, one or more AA batteries, or one or more 9 Volt batteries, for example. Second assembly 200 also includes a switch (not shown) that connects or disconnects the one or more batteries and the second electrical connector to turn on or off the one or more rear-facing light sources and the one or more forward-facing light sources of first assembly 100.

First assembly 100 is physically connected to second assembly 200 through a first detachable connection (not shown) so that second end 122 of shank 120 is physically connected to first end 211 of handle 210 and the first electrical connector is electrically connected to the second electrical connector. The first detachable connection can be any type of physical connection that also allows separation. For example, the first detachable connection can be a tongue and groove connection, where a tongue of first assembly 100 is inserted into a groove of second assembly 200. A latch may be used to secure the connection and can be opened to allow the assemblies to be detached. First assembly 100 is detached from second assembly 200 for sanitizing, for example. In various embodiments, first assembly 110 is watertight and pressure safe so that first assembly 100 can be sanitized by sanitation devices.

Third assembly 300 includes laser pointer 310. Laser pointer 310 directs laser light from first end 311 of laser pointer 310. Laser pointer 310 is useful for directing a patient's attention to a computer screen, for example, when describing a proposed procedure. Third assembly 300 also includes a switch (not shown) that connects or disconnects laser pointer 310 to a fourth electrical connector (not shown) located at second end 312 of laser pointer 310 to turn on or off laser pointer 310.

Third assembly 300 is physically connected to second assembly 200 through a second detachable connection (not shown) so that second end 312 of laser pointer 310 is physically connected to second end 212 of handle 210 and the fourth electrical connector is electrically connected to the third electrical connector. The connection of the fourth electrical connector to the third electrical connector allows laser pointer 310 to receive power from the one or more batteries of second assembly 200. The second detachable connection can also be any type of physical connection that also allows separation. For example, the first detachable connection can be a tongue and groove connection, where a tongue of third assembly 300 is inserted into a groove of second assembly 200. A latch may also be used to secure the connection and can be opened to allow the assemblies to be detached. Third assembly 300 is detached from second assembly 200 to allow other devices to be attached to second assembly 200, for example.

In various embodiments, third assembly 300 further includes a housing for storing a writing device. The writing device can be, for example, pen 320. The writing device can also be a stylus for writing on an electronic device. The writing device allows a dentist to use the mirror to quickly record information about the patient.

Figure 5:
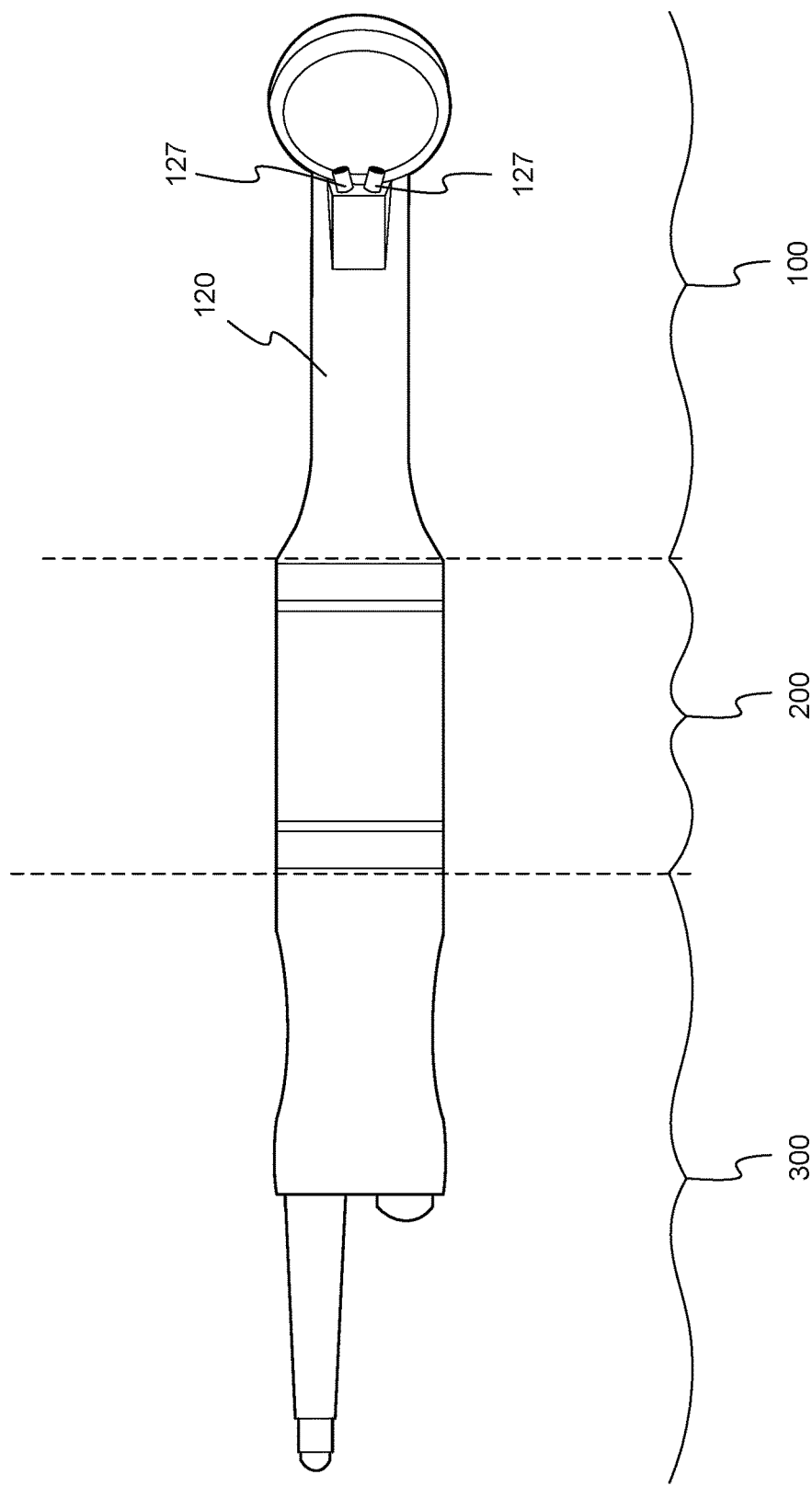
FIG. 5 is a top view of a multipurpose self-illuminating dental mirror, in accordance with various embodiments.

FIG. 5 is a top view 500 of a multipurpose self-illuminating dental mirror, in accordance with various embodiments. First assembly 100, second assembly 200, and third assembly 300 are shown in view 500. One or more forward-facing light sources include two forward-facing light sources 127 in this embodiment. The one or more forward-facing light sources can be one or more light emitting diodes (LEDs), for example.

Figure 6:
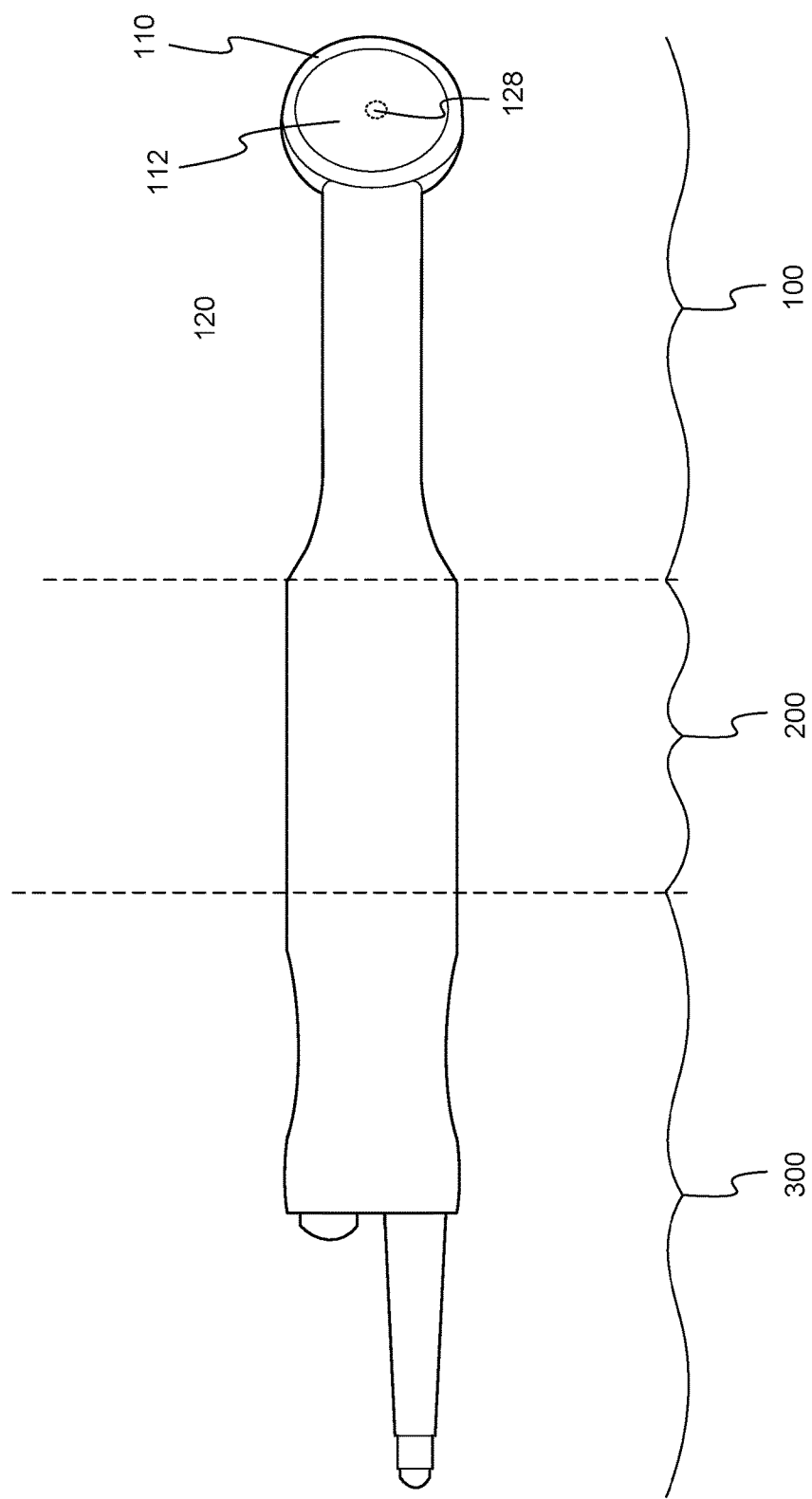
FIG. 6 is a bottom view of a multipurpose self-illuminating dental mirror, in accordance with various embodiments.

FIG. 6 is a bottom view 600 of a multipurpose self-illuminating dental mirror, in accordance with various embodiments. First assembly 100, second assembly 200, and third assembly 300 are shown in view 600. One or more rear-facing light sources include one rear-facing light source 128 in this embodiment. Rear-facing light source 128 is located on head 110 of first assembly 100. Rear-facing light source 128 is located behind rear transparent surface 112 of head 110. Rear transparent surface 112 is clear glass, for example. The one or more rear-facing light sources can be one or more light emitting diodes (LEDs), for example.

FIG. 7 is a perspective view 700 of a multipurpose self-illuminating dental mirror, in accordance with various embodiments. First assembly 100, second assembly 200, and third assembly 300 are shown in view 700. In this embodiment, shank 120 has a rectangular cross-section 130. Further, width 131 of rectangular cross-section 130 of shank 120 is greater than height 132 so that shank 120 can be used to retract a patient's lip or tongue. In this embodiment, handle 210 also has a rectangular cross-section 230.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A multipurpose self-illuminating dental mirror, comprising:
    a first assembly that includes a head having a mirrored forward surface and a rear transparent surface that includes one or more rear-facing light sources, a shank connected at first end to a side of the head and extending longitudinally at an angle from the plane of the head having one or more forward-facing light sources extending from the shank at the connection of the shank with the head, and wiring from the one or more rear-facing light sources and one or more forward-facing light sources that extends through the shank to a first electrical connector at a second end of the shank;
    a second assembly that includes a handle having a housing for one or more batteries, wiring that electrically connects the one or more batteries to a second electrical connector at a first end of the handle and a third electrical connector at a second end of the handle, and a switch that connects or disconnects the one or more batteries and the second electrical connector, wherein in the first assembly is physically connected to the second assembly through a first detachable connection so that the second end of the shank is physically connected to the first end of the handle and the first electrical connector is electrically connected to the second electrical connector; and
    a third assembly that includes a laser pointer that directs laser light from a first end of the laser pointer and a switch that connects or disconnects the laser pointer to a fourth electrical connector located at a second end of the laser pointer, wherein the third assembly is physically connected to the second assembly through a second detachable connection so that the second end of the laser pointer is physically connected to the second end of the handle and the fourth electrical connector is electrically connected to the third electrical connector.

2. The multipurpose self-illuminating dental mirror of claim 1, wherein the one or more rear-facing light sources comprise one or more light emitting diodes (LEDs).

3. The multipurpose self-illuminating dental mirror of claim 1, wherein the one or more forward-facing light sources comprise one or more light emitting diodes (LEDs).

4. The multipurpose self-illuminating dental mirror of claim 1, wherein the cross-section of the shank is rectangular.

5. The multipurpose self-illuminating dental mirror of claim 4, wherein the width of the rectangular cross-section of the shank is greater than the height so that the shank can be used to retract a patient's lip or tongue.

6. The multipurpose self-illuminating dental mirror of claim 1, wherein the cross-section of the handle is rectangular.

7. The multipurpose self-illuminating dental mirror of claim 1, wherein the one or more batteries comprise one or more AAA batteries.

8. The multipurpose self-illuminating dental mirror of claim 1, wherein the one or more batteries comprise one or more AA batteries.

9. The multipurpose self-illuminating dental mirror of claim 1, wherein the one or more batteries comprise one or more 9 Volt batteries.

10. The multipurpose self-illuminating dental mirror of claim 1, wherein the first assembly is watertight and pressure safe so that the first assembly can be sanitized by sanitation devices.

11. The multipurpose self-illuminating dental mirror of claim 1, wherein the third assembly further comprises a housing for storing a writing device.

12. The multipurpose self-illuminating dental mirror of claim 11, wherein the writing device comprises a pen.

13. The multipurpose self-illuminating dental mirror of claim 11, wherein the writing device comprises a stylus for writing on an electronic device.

14. The multipurpose self-illuminating dental mirror of claim 1, wherein the rear transparent surface comprises clear glass.

15. The multipurpose self-illuminating dental mirror of claim 1, wherein one or more forward-facing light sources comprise two forward-facing light sources.

* * * * *